United States Patent [19]

Cherry, III et al.

[11] Patent Number: 4,474,067

[45] Date of Patent: Oct. 2, 1984

[54] SKI MEASURING APPARATUS

[76] Inventors: Howard H. Cherry, III, 1 Oak Park Dr., Bettendorf, Iowa 52722; Stephen C. Wright, R.R. #1, Box 171A, Davenport, Iowa 52806

[21] Appl. No.: 436,243

[22] Filed: Oct. 25, 1982

[51] Int. Cl.³ ............................................. G01N 3/00
[52] U.S. Cl. ...................................... 73/794; 73/849
[58] Field of Search .................. 73/794, 847, 849, 853, 73/852, 851, 161

[56] References Cited

U.S. PATENT DOCUMENTS

| | | | |
|---|---|---|---|
| 1,915,289 | 6/1933 | Broadus | 73/849 |
| 2,426,583 | 9/1947 | Bailey | 73/853 |
| 2,795,953 | 6/1957 | Makowsky | |
| 3,178,937 | 4/1965 | Bradley | |
| 3,400,573 | 9/1968 | Matter | 73/37.5 |
| 3,964,300 | 6/1976 | Howe | 73/849 |
| 4,195,532 | 4/1980 | Pauls | 73/849 |

Primary Examiner—Jerry W. Myracle
Attorney, Agent, or Firm—Henderson & Sturm

[57] ABSTRACT

A ski measuring apparatus for measuring the resistance of a ski to flexing in order to determine the suitability of the ski to a particular user or condition. The apparatus comprises a fixture for supporting a ski in its natural, unloaded condition in such manner that an end portion of the ski projects from a securing device. A force-exerting unit, such as a fluid motor, is activated between the fixture and the cantilevered end of the ski to deflect that end to a predetermined degree, and this degree or a function thereof is measured in order to ascertain the resistance of the ski to such deflection. In a preferred form, the invention provides for the flexing of the ski in bending and also in torsion, in both instances the resistances being measured. These measurements may be taken in any manner or by any form of instrumentation.

11 Claims, 4 Drawing Figures

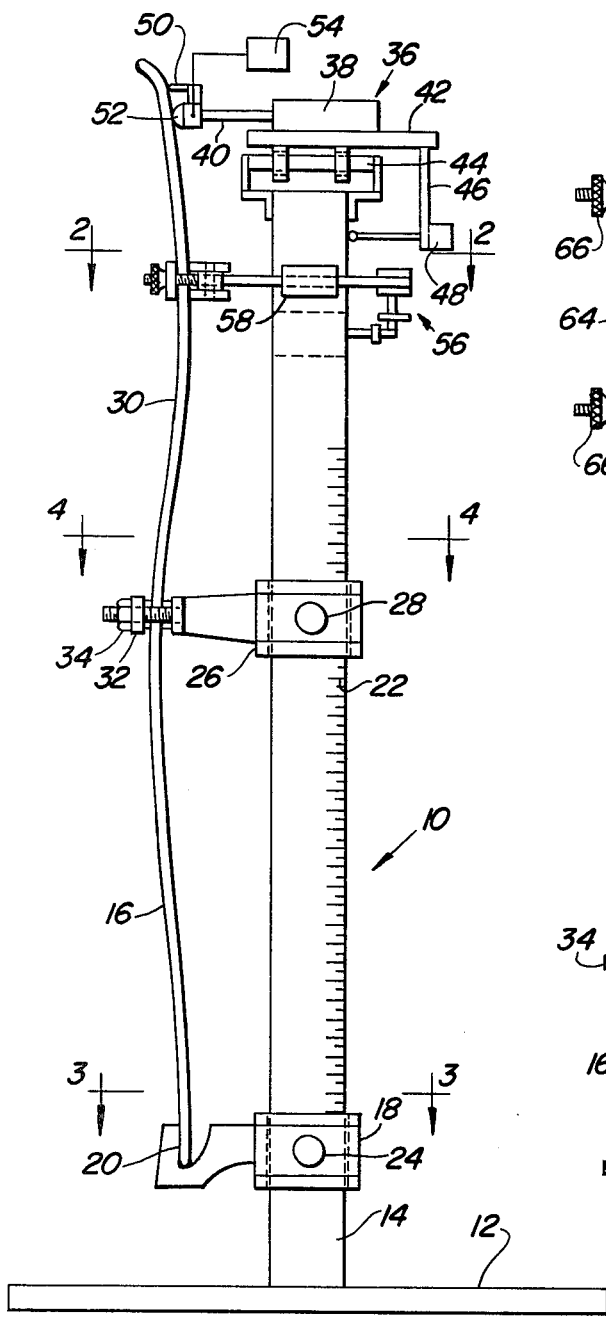
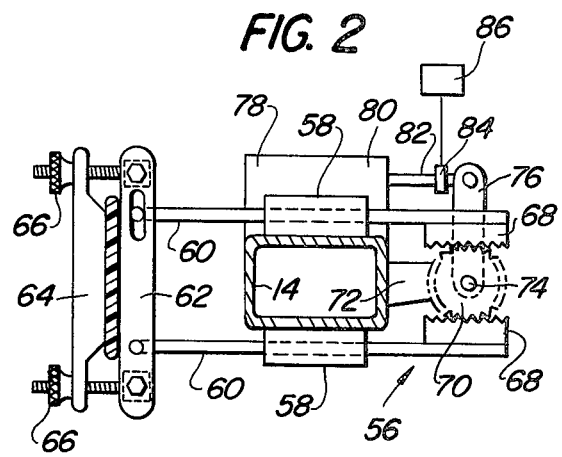
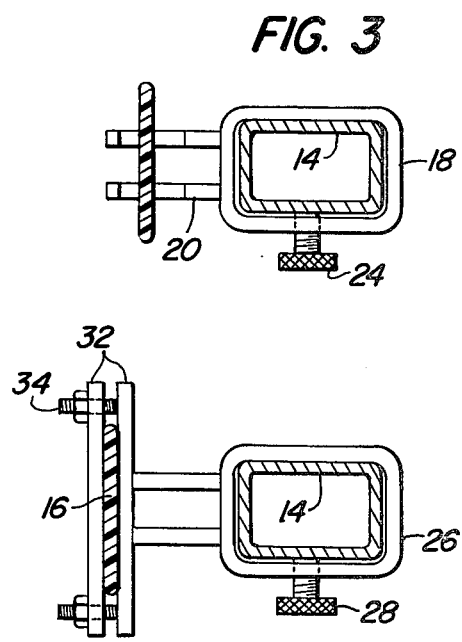
FIG. 1
FIG. 2
FIG. 3
FIG. 4

SKI MEASURING APPARATUS

BACKGROUND OF THE INVENTION

Known apparatus and methods for testing skis for stiffness or resistance to bending function on the principle of placing a pair of skis face-to-face or bottom-to-bottom and then applying forces between the skis. For example, in the U.S. Pat. No. 4,195,532, to Pauls, a C-clamp form of force-applying means is used to squeeze the skis together at midportions thereof and then to read a gage associated with the clamp. In the U.S. Pat. No. 3,964,300, to Howe, the pair of skis are clamped tightly together at their opposed midportions, and then a gage is inserted between the diverging front end portions and a reading taken on the gage. The two forms of prior art just noted have in common the testing of both skis simultaneously and testing for bending stiffness only.

According to the present invention, each ski is tested individually and, further, is tested in torsion as well as in bending, thus enabling a better determination of the suitability of the ski to a particular user and/or to particular conditions expected to be encountered in use. The present apparatus is simple to use and may be inexpensively constructed. It preferably comprises an elongated support alongside which the ski is placed in general parallelism. The support carries a clamp or the like which securely engages a portion of the ski intermediate it ends, leaving one end portion projecting cantilever fashion beyond the clamp. In its simplest form, a fluid motor applies force between the support and the cantilevered end to stress the ski in bending through a preselected amount, and the force exerted by the motor is measured, as by a load cell, for example. This motor is deactivated; and a second motor, for example, engages a lever arm temporarily clamped to the cantilevered portion of the ski; and the motor is extended to stress the ski in torsion about its lengthwise axis. The degree of torsional flexing is preselected, and again a reading is taken of the force exerted by the twisting motor to twist the ski to that degree. The parts associated with the support for engaging the ski are fashioned so the ski may be inverted and both end portions checked as aforesaid.

Further features and advantages of the invention will be seen as the description of a preferred form of the invention progresses.

DESCRIPTION OF THE DRAWINGS

FIG. 1 is an elevation of the fixture, shown with a ski in position to be checked and measurements taken.

FIG. 2 is an enlarged section on the line 2—2 of FIG. 1.

FIG. 3 is an enlarged section on the line 3—3 of FIG. 1.

FIG. 4 is an enlarged section on the line 4—4 of FIG. 1.

DETAILED DESCRIPTION OF THE INVENTION

The preferred fixture is designated as a whole by the numeral 10 and preferably comprises a free-standing base 12 and an upright, elongated support member or column 14 rising from, and rigid with, the base. The base may be of steel plate, and the member or column is preferably of high-strength tubular steel or other appropriate material. The base may be bolted or otherwise attached to the floor.

A typical ski 16 is shown disposed in upright position alongside the column in general parallelism therewith and spaced outwardly therefrom. In this instance, the ski is disposed with its front end upwardly. At this point it should be observed that the illustrated and described geographical attributes (upright, upper, etc.) are used for clarity and brevity and not by way of limitation. The column has at its lower end a holding means 18 which has an upwardly opening pocket 20 for receiving the lower end of the ski. The pocket is shaped, however, in such fashion as to be capable of receiving the front end of the ski when the ski is turned end-for-end. The holding means is preferably in the form of a collar surrounding the column and arranged for selected adjustment vertically or lengthwise of the column, in this case the column having a plurality of lines forming a linear scale 22, and a clamp screw 24 is provided for selective infinite adjustment of the holding means. Thus the holding means is adapted to accept skis of different lengths.

A securing device or clamp 26 is carried by the column above the holding means 18 and, like that means, is in the form of a collar slidable along the column for selective infinite adjustment via the scale 22 and a clamp screw 28, again according to the length of the ski being checked. This clamp engages a portion of the ski intermediate the ends of the ski in such manner as to leave an end portion 30 of the ski projecting in cantilevered fashion from the clamp. The clamp is shown here (FIG. 4) as comprising a pair of cooperative plates 32 removably secured together as by bolts 34 for ease in mounting and dismounting the ski. Of significance is the fact that the ski is held by the holding means 18 and clamp 26 in its natural, unloaded condition, i.e., without any initial deflection. As will be seen, this enables easier and accurate checking of the ski for stiffness and resistance to twisting about its longitudinal dimension.

A force-exerting bending means, denoted in general at 36, is carried at the upper portion of the column in substantially transverse alinement with the free end of the cantilevered portion 30 of the ski. This bending means is here in form of a power unit such as a fluid motor having relatively movable parts, such as a cylinder 38 and piston rod 40. The cylinder is fixed to a carrier 42 which is carried by a slide 44 affixed to the top of the column. The carrier has a depending leg 46 engaged by a column-carried second fluid motor or like power unit 48, reciprocation of which moves the bending motor cylinder selectively back and forth or toward and away from the free end of the ski. The purpose of this arrangement is to selectively position the bending motor so that its piston rod just contacts the free end of the ski; that is, the bending motor has a stroke of predetermined length so that the piston rod will travel away from and back to a starting position. If the bending motor cylinder were fixed to the column, its stroke would not accommodate a ski having a greater front end curvature than that shown. In other words, regardless of what form of ski is to be checked, the present arrangement will enable the same amount of bending because the piston rod will always start with its end in contact with the ski and the stroke will be the same at all times. If desired, a limit switch 50 may be located at the free end of the piston rod 40 so that the adjusting motor 48 will be deactivated when piston-rod-to-ski contact is made. A suitable wiring diagram can be readily devised by those skilled in the art, and the precise details are not significant here.

It will be seen that even though the stroke of the bending motor is fixed and hence the degree of bending of the ski in its cantilevered portion as between the piston rod 40 and clamp 26 will be a function of the stroke of the bending motor, the force exerted by the motor to achieve that amount of bending will vary from ski to ski. A simple way to measure the forces is by use of measuring means such as a typical load cell 52 and a reading taken on a suitable display 54, again details that will be familiar to those skilled in the art of measuring via load cells and the like.

When the bending motor is deactivated, its piston rod will be withdrawn and thus out of contact with the ski. With the bending motor thus situated, the ski may be checked for torsional resistance by force-exerting twisting means denoted as a whole by the numeral 56. This means includes a pair of horizontal slides 58 fixed to the column at a location below the bending means. Each slide carries a rod 60 (FIG. 2) of equal length. The rods are pivotally cross-connected at their ski-approximate ends by a bar 62, and this bar is supplemented by a second bar 64. One bar lies at each side of the ski, and the cantilevered portion 30 of the ski is clamped between the two bars by a pair of releasable means such as screw devices 66. The bars are provided respectively at their ends at the rear of the column with toothed portions or racks 68 which respectively engage diametrically opposed portions of a pinion 70 which is in turn journaled on the column in any suitable manner as at 72. The pinion is keyed or otherwise fixed to a shaft 74 which is fixed to one end of an arm 76. A torsion applying motor 78 is included in the twisting means 56 and again may be a power unit of the fluid motor type having a cylinder 80 and piston rod 82. The cylinder is mounted in any suitable manner on the column, and the free end of the piston rod is connected to the free end of the pinion arm 76 so that reciprocation of the piston rod on a stroke of preselected length rotates the pinion and via the racks applies twisting forces to the ski. The ends of the bars 62 and 64 that project laterally from the ski form lever arms acted on by the rods to which the racks are affixed. It will be recalled that the ski is held by the clamp or securing device 26, and it is the cantilevered part of the ski that will be stressed in torsion. As a means of measuring the force exerted by the twisiting motor, a load cell 84 may be interposed in the piston rod 82 and a readout taken on a display 86. These details are not significant, being within the skill of those familiar with instrumentation for measuring forces, etc.

As noted previously, after measurements are taken with the ski in the position shown, it may be removed, inverted and remounted for taking measurements at the opposite end. Also, because of the adjustability of the means 18 and 26, skis of different lengths may be checked, and changes in position of the clamp 26 relative to the free end of a ski will of course vary the length of the cantilevered portion of the ski.

Features of the invention other than those pointed out above will be apparent to those skilled in the art, as will be many modifications in the preferred form of the invention shown, all of which may be made without departure from the spirit and scope of the invention.

We claim:

1. Ski measuring apparatus, comprising: a rigid fixture; means on the fixture for mounting a ski thereon in its normal, unflexed condition, said means including a securing device for fixedly engaging the ski at a portion thereof intermediate its ends so as to leave one end portion of the ski projecting from said securing device in cantilever fashion and clear of the fixture; force-exerting means engageable between the fixture and the cantilevered end portion of the ski for flexing said end portion relative to the secured portion; and means for measuring the resistance of the cantilevered portion to flexing;

further characterized in that the force-exerting device engages the cantilevered portion in such manner as to flex the cantilevered portion in torsion.

2. Ski measuring apparatus, comprising: a rigid fixture; means on the fixture for mounting a ski thereon in its normal, unflexed condition, said means including a securing device for fixedly engaging the ski at a portion thereof intermediate its ends so as to leave one end portion of the ski projecting from said securing device in cantilever fashion and clear of the fixture; force-exerting means engageable between the fixture and the cantilevered end portion of the ski for flexing said end portion relative to the secured portion; and mean for measuring the resistance of the cantilevered portion to flexing;

further characterized in that the force-exerting device engages the cantilevered portion of the ski in such manner as to flex it in bending; the measuring means measures the resistance of the cantilevered portion to flexing in bending; a second force-exerting device is operative in alternation with the first-named force-exerting device and is engageable with the cantilevered portion in such manner as to flex the cantilevered portion in torsion; and a second means is provided for operation in alternation with the first measuring means for measuring the resistance of the cantilevered portion to flexing in torsion.

3. Ski measuring apparatus, comprising: a rigid fixture; means on the fixture for mounting a ski thereon in its normal, unflexed condition, said means including a securing device for fixedly engaging the ski at a portion thereof intermediate its ends so as to leave one end portion of the ski projecting from said securing device in cantilever fashion and clear of the fixture; force-exerting means engageable between the fixture and the cantilevered end portion of the ski for flexing said end portion relative to the secured portion; and means for measuring the resistance of the cantilevered portion to flexing;

further characterized in that holding means is carried by the fixture for supporting the end of the ski opposite to the cantilevered portion.

4. The apparatus of claim 3, further characterized in that the holding means includes a pocket into which said opposite end of the ski is receivable.

5. The apparatus of claim 4, further characterized in that the pocket is so shaped as to be capable of receiving either end of the ski so that the measured ski may be reversed end-for-end relative to the fixture.

6. Ski measuring apparatus, comprising: a rigid fixture, means on the fixture for mounting a ski thereon in its normal, unflexed condition, said means including a securing device for fixedly engaging the ski at a portion thereof intermediate its ends so as to leave one end portion of the ski projecting from said securing device in cantilever fashion and clear of the fixture; force-exerting means engageable between the fixture and the cantilevered end portion of the ski for flexing said end portion relative to the secured portion; and means for measuring the resistance of the cantilevered portion to flexing;

further characterized in that the force-exerting means is a power unit including a first part engageable with the cantilevered end portion of the ski and a second part mountable on the fixture, said first part being movable relative to the fixture and ski for varying the locus of the starting position according to selected characteristics of the ski to be measured.

7. The apparatus of claim 6, further characterized in that the power unit is a fluid motor and one of the parts is a cylinder and the other part is a piston.

8. The apparatus of claim 6, further characterized in that a second power unit is connected between the fixture and the adjustable part of the first-named power unit for effecting adjustment of said part.

9. Ski measuring apparatus, comprising: a rigid fixture; means on the fixture for mounting a ski thereon in its normal, unflexed condition, said means including a securing device for fixedly engaging the ski at a portion thereof intermediate its ends so as to leave one end portion of the ski projecting from said securing device in cantilever fashion and clear of the fixture; force-exerting means engageable between the fixture and the cantilevered end portion of the ski for flexing said end portion relative to the secured portion; and means for measuring the resistance of the cantilevered portion to flexing;

further characterized in that the fixture is in the form of an elongated support alongside which the ski is placed with its length substantially paralleling that of the member, and the securing device and force-exerting means are mounted on the member in longitudinally spaced apart relation.

10. The apparatus of claim 9, further characterized in that the securing device is selectively adjustable lengthwise of the member and ski to accommodate skis of different lengths.

11. Ski measuring apparatus, comprising: a rigid fixture; means on the fixture for mounting a ski thereon in its normal, unflexed condition, said means including a securing device for fixedly engaging the ski at a portion thereof interemdiate its ends so as to leave one end portion of the ski projecting from said securing device in cantilever fashion and clear of the fixture; force-exerting means engageable between the fixture and the cantilevered end portion of the ski for flexing said end portion relative to the secured portion; and means for measuring the resistance of the cantilevered portion to flexing;

further characterized in that the force-exerting means includes an element engageable with the cantilevered portion as a lever arm projecting laterally from the ski and the force exerted by the force-exerting means acts on the lever arm to flex the cantilevered ski portion in torsion.

* * * * *